United States Patent [19]

Cills

[11] Patent Number: 4,652,237
[45] Date of Patent: Mar. 24, 1987

[54] DENTAL IMPRESSION TRAY

[76] Inventor: Howard R. Cills, 21 Oriole Way, Moorestown, N.J. 08057

[21] Appl. No.: 848,418

[22] Filed: Apr. 4, 1986

[51] Int. Cl.[4] .............................................. A61C 9/00
[52] U.S. Cl. ........................................ 433/37; 433/38
[58] Field of Search .................................... 433/37, 36

[56] References Cited

U.S. PATENT DOCUMENTS 2,428,773 10/1947 Beresin et al. ...................... 433/36
3,722,097 3/1973 Coleman et al. ..................... 433/36

Primary Examiner—Robert Peshock
Attorney, Agent, or Firm—Caesar, Rivise, Bernstein, Cohen & Pokotilow, Ltd.

[57] ABSTRACT

This invention relates to a dental impression tray having a U-shaped rim that can be positioned about the upper teeth of a patient. The upper posterior end of the impression tray is closed by a dam made of a preferably pliable material. Openings are provided in the U-shaped rim to permit the escape of hardenable material that may be placed under pressure as the dentist moves the impression tray into proper position in order to obtain the necessary impression of the upper teeth. The dam prevents unwanted posterior flow of the hardenable material into the throat of a patient.

1 Claim, 4 Drawing Figures

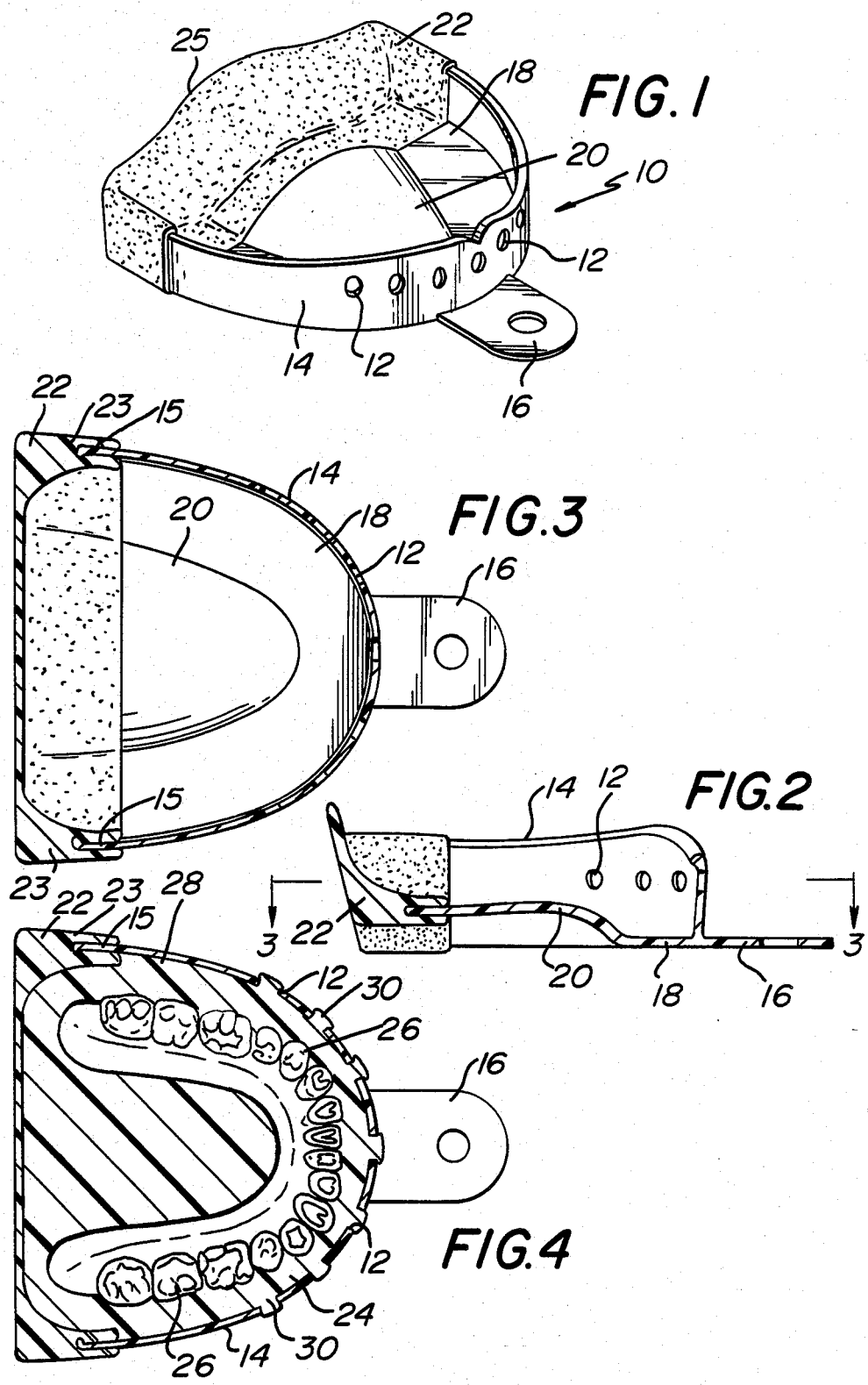

DENTAL IMPRESSION TRAY

BACKGROUND OF THE INVENTION

This invention relates to a dental impression tray and has as its principal objective the provision of a new and improved dental impression tray of this general case.

Dental impression trays are now in wide use in order to produce the necessary model of the upper teeth of a patient. Such model is used by the dentist or a dental technician in the preparation of various dental devices, such as a bridge.

It has been determined that considerable care and skill is required on the part of the dentist when a hardenable material is introduced into the impression tray and the impression tray is then brought into contact with the upper teeth of a patient. This is because it is generally the practice to use a slight excess of hardenable material in the impression tray to be sure that there will be sufficient hardenable material so that a proper impression will be formed. Unfortunately the use of even a slight excess of hardenable material creates the possibility that certain of such material will flow posteriorly or will back-up into the throat of a patient. This problem is compounded because of the natural variations in the teeth disposition and spacing in various patients. Thus, it is very difficult to introduce exactly the correct amount of hardenable material into the impression tray or even to control the amount of the slight excess.

Examples of prior impression trays can be found in Osgood U.S. Pat. No. 637,480 as well as Canadian Pat. No. 950,246 and West German Pat. No. 1,952,731. In the Osgood patent there is shown a dental impression cup having a retaining wall that is fitted with an elastic body portion. However, the Osgood cup does not have any provision to allow anterior escape of excess hardenable material, as with the present invention.

It is accordingly an object of the present invention to provide an improved dental impression tray that will substantially lessen the chances of posterior escape of the hardenable material.

Yet another object of the present invention is to provide an impression tray that can be manufactured at low cost using readily available materials.

Other objects and many of the attendant advantages of this invention will be readily appreciated when the same becomes better understood by reference to the following detailed description when considered in connection with the accompanying drawings wherein:

FIG. 1 is a three dimensional view showing a preferred embodiment of the dental impression tray of the present invention;

FIG. 2 is a sectional view of the maxillary impression tray of FIG. 1;

FIG. 3 is a sectional view taken along the line 3—3 of FIG. 2; and

FIG. 4 is a sectional view, similar to FIG. 3, but showing the relationship of the dental impression tray, the upper teeth and the hardenable material which has been introduced into the impression tray.

Referring now in greater detail to the various figures of the drawings wherein like references characters refer to like parts there is shown in FIG. 1 the impression tray 10 of the present invention includes the elements of a conventional impression tray that is in wide use today.

What the present invention provides in the preferred embodiment of the invention is a slidable dam 22 that prevents the hardenable material 28 from extruding posteriorly. The preferred embodiment also has a series of relief openings 12 in the U-shaped rim 14 that allow the displaced material to extrude anteriorly as shown in FIG. 1.

It will also be seen from FIG. 1 that a handle 16 projects outwardly from the rim 14 to enable the dentist to grasp and maneuver the impression tray into proper position in the mouth of a patient in order to obtain an impression of the upper teeth while minimizing the gagging that may occur.

The impression tray 10 further includes a floor 18 from which a convex area 20 projects upwardly in a conventional fashion.

The open end of the impression tray 10 is enclosed by a dam 22, with curved ends 23 each of which is secured to rim 14 by means of a suitable adhesive. The dam 22 is made of a pliable plastic material and thus the ends 15 of rim 14 can be readily inserted into the curved ends 23. The adhesive may be applied to ends 15 either before or after a cut or slit has been made in the curved ends 23 or they may be precut to receive the adhesively coating ends 15.

It should be noted that the various materials used in the manufacture of the present invention may be plastic or metal or a combination of plastic or metal, depending upon the level of technology as well as other factors such as desired weight of the impression tray and appearance.

In the preferred embodiment of the invention the dam 22 is made of a pliable plastic material, such as a vinyl plastic with the rim 14, the floor 18 with the convex area 20, and the handle all being made of metal or molded plastic.

In use the dentist first fills the area defined by the floor 18 and the rim 12 with hardenable material 24 which will function to accept and hold the impression of the upper teeth 26 of the patient.

The impression tray 10 is then inserted carefully in the patient's mouth and brought into contact with the upper teeth and gums of the patient by seating the dam so that it is in contact with the palate and rotating the tray anteriorly and superiorly such that the hardenable material 24 will flow into contact with the upper teeth 26 and about the upper teeth 26. The contact by the dam against the palate prevents unwanted posterior flow of the hardenable material.

As the dentist presses the filled impression tray against the patient's teeth, and gums in order to obtain the impression of the upper teeth, any excess hardenable material 28 placed under pressure by the movement of the impression tray into place can readily escape at 30 through the openings 12 in the rim 14. Thus, the tendency of hardenable material 24 to attempt to back out above the dam and into the patient's throat, is lessened.

While the preferred embodiment herein disclosed has a U-shaped rim, it is contemplated that the rim may be four sided or fully closed so that the back wall of the rim will function as the dam. Such a rim may be pliable or non-pliable, as desired. In all cases, however, the rim will possess anteriorly located openings so that flow of the hardenable material will be through these openings and forwardly in the direction of handle 16.

Without further elaboration, the foregoing will so fully illustrate my invention that others may, by applying current or future knowledge, readily adopt the same for use under various conditions of service.

I claim:

1. A U-shaped maxillary dental impression tray including a U-shaped rim that is adapted to be positioned about the teeth and palate of a patient, said rim extending from a base, with said impression tray being open upwardly, and said U-shaped rim also having an open end which is closed by a pliable dam attached to said rim, said impression tray including a forward section located anteriorly of a patient's front teeth, said forward section having at least one opening whereby excess hardenable material introduced into said impression tray will be contained by said rim dam and said base, and may flow anteriorly through said opening to prevent posterior flow of said hardenable material into the mouth of a patient, and wherein said pliable dam is urged against the patient's palate to prevent unwanted posterior flow of said hardenable material.

* * * * *